United States Patent [19]

Faler et al.

[11] Patent Number: 4,701,566
[45] Date of Patent: Oct. 20, 1987

[54] METHOD FOR PREPARING SPIROBIINDANE BISPHENOLS

[75] Inventors: Gary R. Faler; Jerry C. Lynch, both of Scotia, N.Y.

[73] Assignee: General Electric Company, Schenectady, N.Y.

[21] Appl. No.: 917,645

[22] Filed: Oct. 10, 1986

[51] Int. Cl.$^4$ ............................................. C07C 39/17
[52] U.S. Cl. ................................... 568/719; 568/729
[58] Field of Search ............................... 568/719, 729

[56] References Cited

U.S. PATENT DOCUMENTS 4,605,789  8/1986  Silvis et al. ........................... 568/719

Primary Examiner—Werren B. Lone
Attorney, Agent, or Firm—William H. Pittman; James C. Davis, Jr.; James Magee, Jr.

[57] ABSTRACT

Spirobiindane bisphenols are prepared by contacting a mixture of a bisphenol or a 4-isopropenylphenol and a 1-(4-hydroxyphenyl)indanol with a metal halide Lewis acid or an alkanesulfonic acid. High purity spirobiindane bisphenols may be prepared by employing a purification sequence, which preferably includes a step of precipitation of the product with water from a methanol-methylene chloride solution.

20 Claims, No Drawings

METHOD FOR PREPARING SPIROBIINDANE BISPHENOLS

This invention relates to the preparation of spirobiindane bisphenols.

Spirobiindane bisphenols of the formula

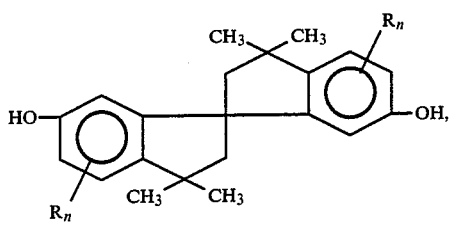

wherein each R is independently $C_{1-4}$ primary or secondary alkyl or halo and n is from 0 to 3 and methods for their preparation have been known for some time. The prior art also discloses their conversion to polycarbonates and other polymers. In addition, compositions comprising cyclic polycarbonate oligomers of spirobiindane bisphenols are disclosed and claimed in copending, commonly owned application Ser. No. 887,503, filed July 21, 1986, and are shown to possess unique and advantageous properties.

The preparation of spirobiindane bisphenols by the condensation of bisphenols or isopropenylphenols in the presence of acidic catalysts is disclosed in various references. For example, Baker et al., *J. Chem. Soc.*, 1421–1424 (1939), describes the preparation of a compound of formula I in which R is methyl and n is 1 by the reaction of 2,2-bis(3-methyl-4-hydroxyphenyl)propane with concentrated hydrochloric acid. A similar reaction of 2,2-bis(4-hydroxyphenyl)propane, or bisphenol A, is disclosed in Curtis, *J. Chem. Soc.*, 415–418 (1962).

U.S. Pat. No. 2,979,534 describes the conversion of bisphenols such as bisphenol A to 1-(4-hydroxyphenyl)indanols by means of aromatic sulfonic acids such as benzenesulfonic or p-toluenesulfonic acid or mineral acids such as sulfuric acid. It was later found that the principal products were the corresponding spirobiindane bisphenols; Stueben, *J. Poly Sci.*, Part A, 3, 3209–3217 (1965). The preparation of compounds of this type of condensation of bisphenol A in the presence of sulfuric acid is also described in U.S. Pat. No. 3,271,463, in the presence of anhydrous methanesulfonic acid or hydrochloric acid in U.S. Pat. No. 4,552,949, and in the presence of strong acid cation exchange resins in U.S. Pat. No. 4,605,789.

In copending, commonly owned application Ser. No. 917,644, filed Oct. 10, 1986, there is disclosed a method of spirobiindane bisphenol preparation by condensation of a bisphenol or an isopropenylphenol in the presence of an acidic catalyst selected from the group consisting of alkanesulfonic acids and polyvalent metal halides which are strong Lewis acids. By this method, the desired spirobiindane bisphenol is generally obtained in admixture with a 1-(4-hydroxyphenyl)indanol as by-product. The 1-(4-hydroxyphenyl)indanol is in essence a dimer of the isopropenylphenol, the latter either being a reactant or an intermediate obtained by cracking of the bisphenol. For example, 6,6'-dihydroxy-3,3,3',3'-tetramethyl-1,1'-spirobiindane (hereinafter "SBI") is obtained in admixture with 1-(4-hydroxyphenyl)-1,3,3-trimethyl-6-indanol.

The present invention provides a method for increasing spirobiindane bisphenol yield at the expense of 1-(4-hydroxyphenyl)indanol by-product. Said method may be combined with various purification steps for the preparation of high purity spirobiindane bisphenol, suitable for polycarbonate preparation.

Accordingly, the invention in its broadest sense is a method for preparing a spirobiindane bisphenol of formula I which comprises heating a mixture of (A) at least one of bisphenols of the formula

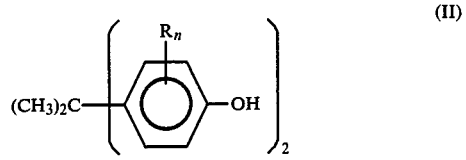

and isopropenylphenols of the formula

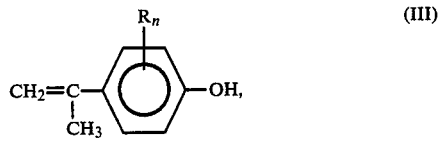

and (B) a 1-(4-hydroxyphenyl)indanol of the formula

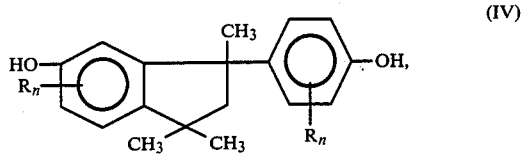

wherein R and n are as previously defined, at a temperature in the range of about 100°–200° C. with an acidic catalyst selected from the group consisting of alkanesulfonic acids and polyvalent metal halides which are strong Lewis acids.

The spirobiindane bisphenols of formula I which may be produced by the method of this invention include SBI, which is usually preferred. Also included are various alkyl- or halo-substituted analogs of SBI, especially those in which n is 1 or 2 and R is methyl, chloro or bromo.

The reactants useful as reagent A include bisphenols of formula II. Illustrative bisphenols are bisphenol A, 2,2-bis(3,5-dibromo-4-hydroxyphenyl)propane, 2,2-bis(3,5-dimethyl-4-hydroxyphenyl)propane and 2,2-bis(3-methyl-4-hydroxyphenyl)propane. The corresponding isopropenylphenols of formula III, or mixtures of bisphenols and isopropenylphenols, may also be used. The preferred compounds are bisphenol A and p-isopropenylphenol. The latter compound may be obtained by cracking of by-product streams from the preparation of bisphenol A or, as previously noted, from bisphenol A itself.

Reagent B is a 1-(4-hydroxyphenyl)indanol of formula IV, generally corresponding in structure to reagent A with respect to the identity and number of R values. Since such 1-(4-hydroxyphenyl)indanols are frequently obtained as by-products in the conversion of the bisphenol or isopropenylphenol to spirobiindane bisphenol, it is within the scope of the invention to employ the crude product from such conversion, in admixture with additional bisphenol and/or isopropenylphenol.

The stoichiometry of the reaction requires at least one mole of reagent A per mole of reagent B for complete conversion of the latter to spirobiindane bisphenol. Therefore, the molar ratio of reagent A to reagent B should generally be at least 1:1 and preferably at least about 1.5:1. However, less than equimolar amounts of reagent A may be employed with the understanding that incomplete conversion of reagent B to spirobiindane bisphenol will be achieved.

The reagent mixture is heated in the presence of an acidic catalyst which may be an alkanesulfonic acid. The preferred alkanesulfonic acids are those containing $C_{1-4}$ primary or secondary alkyl groups, illustrated by methyl, ethyl, 2-propyl and 1-butyl. Methanesulfonic acid is especially preferred by reason of its availability and effectiveness.

Also useful as catalysts are the polyvalent metal halides which are strong Lewis acids. These are generally identical to the metal halides classed as "very active" Friedel-Crafts catalysts in Olah et al., *J. Am. Chem. Soc.*, 94, 7448–7461 (1972). Those halides are $AlCl_3$, $AlBr_3$, $AlI_3$, $GaCl_2$, $GaCl_3$, $GaBr_3$, $GaI_3$, $ZrCl_4$, $HfCl_4$, $HfBr_4$, $HfI_4$, $SbF_5$, $NbF_5$, $NbCl_5$, $TaF_5$, $TaCl_5$, $TaBr_5$, $MoF_6$ and $MoCl_5$. For reasons of availability and effectiveness, the aluminum halides are preferred, with aluminum chloride being most preferred.

As between methanesulfonic acid and aluminum chloride, the factor is usually most preferred by reason of its effectiveness for the production of spirobiindane bisphenols in high yield and particularly high purity. However, aluminum chloride requires a very short reaction time and may be used when some sacrifice in yield and purity is tolerable for the sake of rapid completion.

The reaction is conducted at temperatures within the range of about 100°–200° C., preferably about 125°–175° C. It may be conducted in the melt or in solution in a suitable relatively high boiling organic medium such as phenol, o-dichlorobenzene or 1,2,4-trichlorobenzene.

The proportion of acidic compound, based on the mixture of reagents A and B, is not critical and may be, for example, within the range of about 0.3–10% by weight. The preferred range is about 1–5%. Below 0.5% the reaction rate may drop off sharply. On the other hand, little or no advantage has been detected in the use of amounts above 5%.

The time required for completion of the reaction is generally no greater than about 6 hours, although longer reaction times may be employed with no noticeable decrease in product yield. As previously noted, the reaction is complete somewhat earlier when aluminum chloride is used as a catalyst than when an alkanesulfonic acid is used.

It is possible to isolate spirobiindane bisphenol in sufficient purity for some purposes from the reaction mixture after the procedure described hereinabove. However, for many purposes, including the preparation of high molecular weight polycarbonates, further purification may be necessary. Maximum purity may be attained by a two-step purification sequence which includes the steps of:

(I) removing a major proportion of the by-products and impurities, including phenols of the formula

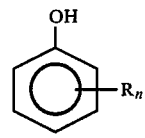

and unreacted 1-(4-hydroxyphenyl)indanols of formula IV, from the crude spirobiindane bisphenol; and (II) further purifying the product of step I by dissolution in a mixture of methanol and methylene chloride followed by precipitation by addition of water.

The impurities present in highest proportion are the above-listed phenols of formula V and unreacted 1-(4-hydroxyphenyl)indanols of formula IV; in SBI preparation, phenol and 1-(4-hydroxyphenyl)-1,3,3-trimethyl-6-indanol.

Phenols, especially phenol itself, may be conveniently removed by simple water washing and/or steam distillation. Removal of unreacted 1-(4-hydroxyphenyl)indanols may be achieved by dissolution in an organic liquid which is a solvent therefor but which does not dissolve the spirobiindane bisphenol in major amounts. Such liquids include aromatic hydrocarbons (e.g., benzene, toluene) and chlorinated aliphatic hydrocarbons (e.g., methylene chloride, chloroform, 1,1,2,2-tetrachloroethane). Methylene chloride is preferred.

Stage II of the purification is effected by dissolving the crude product in a mixture of methanol and methylene chloride, and adding water to precipitate the substantially pure spirobiindane bisphenol. Very little product loss is observed in this step, since the only materials which are removed are color bodies and other impurities which, although present in extremely minor amount, may have a profound effect on the conversion of the spirobiindane bisphenol to polycarbonate and especially on the molecular weight of the polycarbonate.

The proportions of methanol, methylene chloride and water used in stage II are not critical, and may be adjusted as desired to effect the desired dissolution and precipitation. In general, a volume ratio of methanol to methylene chloride of about 3–6:1 and a volume ratio of water to total methanol and methylene chloride of about 0.8–1.2:1 are suitable.

During the dissolution operation of stage II, a homogeneous solution is formed. Upon addition of water, this is converted into a heterogeneous mixture containing liquid and solid phases. Frequently, two liquid phases and one solid phase are present, the latter being the desired purified spirobiindane bisphenol which resides predominantly in a lower methylene chloride liquid phase. The product may be removed by conventional filtration or centrifugation procedures and, if desired, may be washed with a suitable organic liquid such as methylene chloride and dried at elevated temperature and/or reduced pressure. If desired, stage II may be repeated to obtain material of particularly high purity.

The method of this invention is illustrated by the following examples.

EXAMPLE 1

A mixture of 5 grams (21.9 mmol.) of bisphenol A, 3 grams (11.2 mmol.) of 1-(4-hydroxyphenyl)-1,3,3-trimethyl-6-indanol and 250 mg. of methanesulfonic acid was heated for 4 hours at 140° C. in a nitrogen atmosphere. Upon analysis by high pressure liquid chromatography, the mixture was found to contain 7.0 mmol. of SBI.

In a first control experiment, the reaction was conducted identically with the omission of the 1-(4-hydroxyphenyl)-1,3,3-trimethyl-6-indanol. The product was found to contain only 4.95 mmol. of SBI. A second control employed a reaction mixture from which the bisphenol A was omitted, and produced no SBI. Thus, it is seen that 1-(4-hydroxyphenyl)indanols can be converted to spirobiindane bisphenols by the method of this invention.

EXAMPLE 2

A crude product obtained as described in Example 1 is dissolved in a mixture of 8 ml. of methanol and 2 ml. of methylene chloride, forming a homogeneous solution. Deionized water, 10 ml., is added to the solution with stirring, whereupon a heterogeneous mixture is formed. This mixture is filtered and the residue washed with methylene chloride. The methylene chloride-methanol-water dissolution and precipitation step is repeated and the solid product therefrom, consisting of substantially pure SBI, is dried in an oven under vacuum.

What is claimed is:

1. A method for preparing a spirobiindane bisphenol of the formula

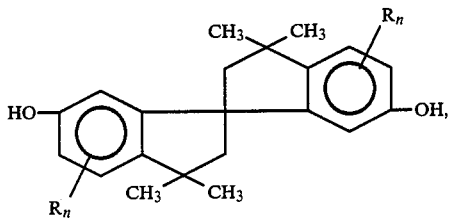

wherein each R is independently $C_{1-4}$ primary or secondary alkyl or halo and n is from 0 to 3, which comprises heating a mixture of (A) at least one of bisphenols of the formula

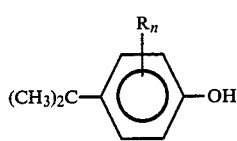

and isopropenylphenols of the formula

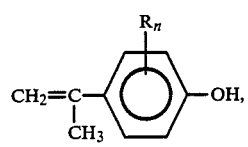

and (B) a 1-(4-hydroxyphenyl)indole of the formula

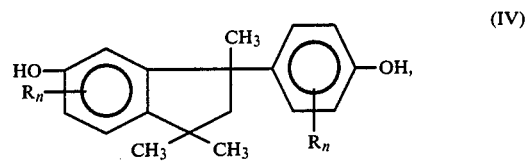

wherein R and n are as previously defined, at a temperature in the range of about 100°–200° C. with an acidic catalyst selected from the group consisting of alkanesulfonic acids and polyvalent metal halides which are strong Lewis acids.

2. A method according to claim 1 wherein the catalyst is an alkanesulfonic acid.
3. A method according to claim 2 wherein the alkanesulfonic acid is methanesulfonic acid.
4. A method according to claim 3 wherein n is 0.
5. A method according to claim 4 wherein the molar ratio of reagent A to reagent B is at least 1:1.
6. A method according to claim 5 wherein reagent A is bisphenol A.
7. A method according to claim 5 wherein reagent A is 4-isopropenylphenol.
8. A method according to claim 1 wherein the catalyst is a metal halide selected from the group consisting of $AlCl_3$, $AlBr_3$, $AlI_3$, $GaCl_2$, $GaCl_3$, $GaBr_3$, $GaI_3$, $ZrCl_4$, $HfCl_4$, $HfBr_4$, $HfI_4$, $SbF_5$, $NbF_5$, $NbCl_5$, $TaF_5$, $TaCl_5$, $TaBr_5$, $MoF_6$ or $MoCl_5$.
9. A method according to claim 8 wherein the metal halide is aluminum chloride.
10. A method according to claim 1 wherein stage A is conducted in the melt.
11. A method according to claim 1 wherein stage A is conducted in solution.
12. A method according to claim 1 which includes the steps of:
(I) removing a major proportion of the by-products and impurities, including phenols of the formula

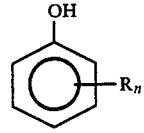

and unreacted 1-(4-hydroxyphenyl)indanols of formula IV, from the crude spirobiindane bisphenol; and
(II) further purifying the product of step I by dissolution a mixture of methanol and methylene chloride followed by precipitation by addition of water.
13. A method according to claim 1 wherein phenols of formula V are removed by at least one of water washing and steam distillation.
14. A method according to claim 12 wherein 1-(4-hydroxyphenyl)indanols of formula IV are removed by dissolution in an organic liquid which is a solvent therefor but which does not dissolve the spirobiindane bisphenol in major amounts.
15. A method according to claim 13 wherein the organic liquid is methylene chloride.
16. A method according to claim 13 wherein the volume ratio of methanol to methylene chloride in stage II is about 3–6:1 and the volume ratio of water to total methanol and methylene chloride is about 0.8–1.2:1.
17. A method according to claim 14 wherein n is 0.
18. A method according to claim 17 wherein the molar ratio of reagent A to reagent B is at least 1:1.
19. A method according to claim 18 wherein reagent A is bisphenol A.
20. A method according to claim 18 wherein reagent A is 4-isopropenylphenol.

* * * * *